United States Patent
Tankovich et al.

(10) Patent No.: US 6,613,040 B2
(45) Date of Patent: Sep. 2, 2003

(54) TWIN LIGHT LASER

(76) Inventors: Nikolai Tankovich, 9301 Stargaze Ave., San Diego, CA (US) 92129; Alexie Lukashev, 3574 Caminito El Rincon #97, San Diego, CA (US) 92130

( * ) Notice: Subject to any disclaimer, the term of this patent is extended or adjusted under 35 U.S.C. 154(b) by 0 days.

(21) Appl. No.: 09/825,516

(22) Filed: Apr. 3, 2001

(65) Prior Publication Data

US 2002/0002367 A1 Jan. 3, 2002

Related U.S. Application Data

(63) Continuation-in-part of application No. 09/608,020, filed on Jun. 30, 2000.

(51) Int. Cl.$^7$ ................................................ A61B 18/20
(52) U.S. Cl. .................................. 606/3; 606/9; 606/10; 606/16
(58) Field of Search ....................... 606/3, 9, 10, 16–18

(56) References Cited

U.S. PATENT DOCUMENTS 5,910,140 A * 6/1999 Shen et al. ..................... 606/3

* cited by examiner

*Primary Examiner*—Lee Cohen
*Assistant Examiner*—H M. Johnson
(74) *Attorney, Agent, or Firm*—John R. Ross; John R. Ross, III (57) ABSTRACT

A laser system in which the gain medium is an excited YAP:Nd crystal. The system is configured so that the crystal produces a twin laser beam comprising wavelengths at both 1079 nm and 1340 nm with substantial intensities at each wavelength. Optical components are described which establish the desired ratio of the intensities of the light at each of the two wavelengths. These ratios, $I_{1079\ nm}/I_{1340\ nm}$, may vary from about 0.1 to 10. In a preferred embodiment of the invention a kit including a YAP:Nd crystal and a specially coated output coupler is provided for converting an existing Nd:YAG laser system to a twin light laser capable of producing the above described twin laser beam. In another embodiment a special combination output coupler is provided which contains at least three partially reflecting mirror elements, one coated to reflect a substantial fraction of light at 1079 nm and pass light at 1340 nm, another mirror coated to reflect a substantial fraction of light at 1340 nm and pass light at 1079 nm and a third mirror coated to reflect a substantial fraction of light at both wavelengths.

7 Claims, 7 Drawing Sheets

TWIN LIGHT LASER

This invention relates to laser systems and in particular to multi-wavelength laser systems. This is a continuation-in-part application of Ser. No. 09/608,020 filed Jun. 30, 2000.

BACKGROUND OF THE INVENTION

Use of lasers for medical purposes is well established. Lasers are used extensively for cosmetic purposes such as hair removal, vein treatment, skin rejuvenation, treatment of telangiectasia and treatment of port wine stain. Each of these treatments is preferably performed with a laser producing laser pulses at a wavelength chosen to be most effective for the particular treatment. For example, a Nd:YAG laser operating at 1064 nm may be used for hair removal and certain types of vein treatment. A Nd:YAG laser operating at 1320 nm may be used for skin rejuvenation and micro skin surgery. Treatment of port wine stains is usually performed using a dye laser operating at a wavelength of 577 nm. Lasers used for treatment of small surface veins do not work very well for treatment of larger deeper veins. As a consequence a medical facility offering a variety of laser-based cosmetic services in the past has been required to acquire and maintain several separate laser systems. This is expensive.

Some wavelengths are very preferentially absorbed in a particular type of tissue such as when the tissue contains a particular chromophore that has a peak or relatively high absorption at the particular wavelength. Use of a laser beam matched to a peak or relatively high absorption in tissue to treat the tissue is referred to as "selective thermolysis". Some wavelengths are absorbed relatively uniformly in tissue and when these wavelengths are used to treat the tissue it is referred to as "non-selective thermolysis" or "homogeneous thermolysis".

What is needed is a single laser that can produce simultaneously laser light at a variety of wavelengths needed in medical facilities specializing is cosmetic care.

SUMMARY OF THE INVENTION

The present invention provides a laser system in which the gain medium is an excited YAP:Nd crystal. The system is configured so that the crystal produces a twin laser beam comprising wavelengths at both 1079 nm and 1341 nm with substantial intensities at each wavelength. Optical components are described which establish the desired ratio of the intensities of the light at each of the two wavelengths. These ratios, $I_{1079\ nm}/I_{1340\ nm}$, may vary from about 0.1 to 10. In a preferred embodiment of the invention a kit including a YAP:Nd crystal and a specially coated output coupler is provided for converting an existing Nd:YAG laser system to a twin light laser capable of producing the above described twin laser beam. The Nd:YAG laser system is unable to produce simultaneously 1064 nm and 1320 nm at substantial intensities of both wavelengths. In another embodiment a special combination output coupler is provided which contains at least three partially reflecting mirror elements, one coated to reflect a substantial fraction of light at 1079 nm and pass light at 1340 nm, another mirror coated to reflect a substantial fraction of light at 1340 nm and pass light at 1079 nm and a third mirror coated to reflect a substantial fraction of light at both wavelengths. In one embodiment the mirror elements are mounted on a rotating frame so that the desired mirror element can be in the beam path to define the resonant cavity. By switching between mirrors the laser operator is able to produce laser beams at 1079 nm, 1340 nm or to produce a beam at a both wavelengths. A preferred embodiment produces a pulsed laser beam capable of providing fluences on the skin surface in the range of about 10 $J/cm^2$ to 200 $J/cm^2$ during a treatment period of less than 4 seconds.

A preferred application of this laser system is aesthetic medicine in which the two wavelength beam illuminates the skin and heats the skin relatively uniformly to a depth of a few millimeters. The skin surface is cooled during the process to prevent or minimize surface tissue damage while tissue beneath the surface is altered due to thermal effects.

This application also discloses techniques for producing other wavelengths from the two wavelength light produced by the YAP:Nd crystal.

DETAILED DESCRIPTION OF PREFERRED EMBODIMENTS

Preferred embodiments of the present invention may be described by reference to the drawings.

First Preferred Embodiment

Figure 1:
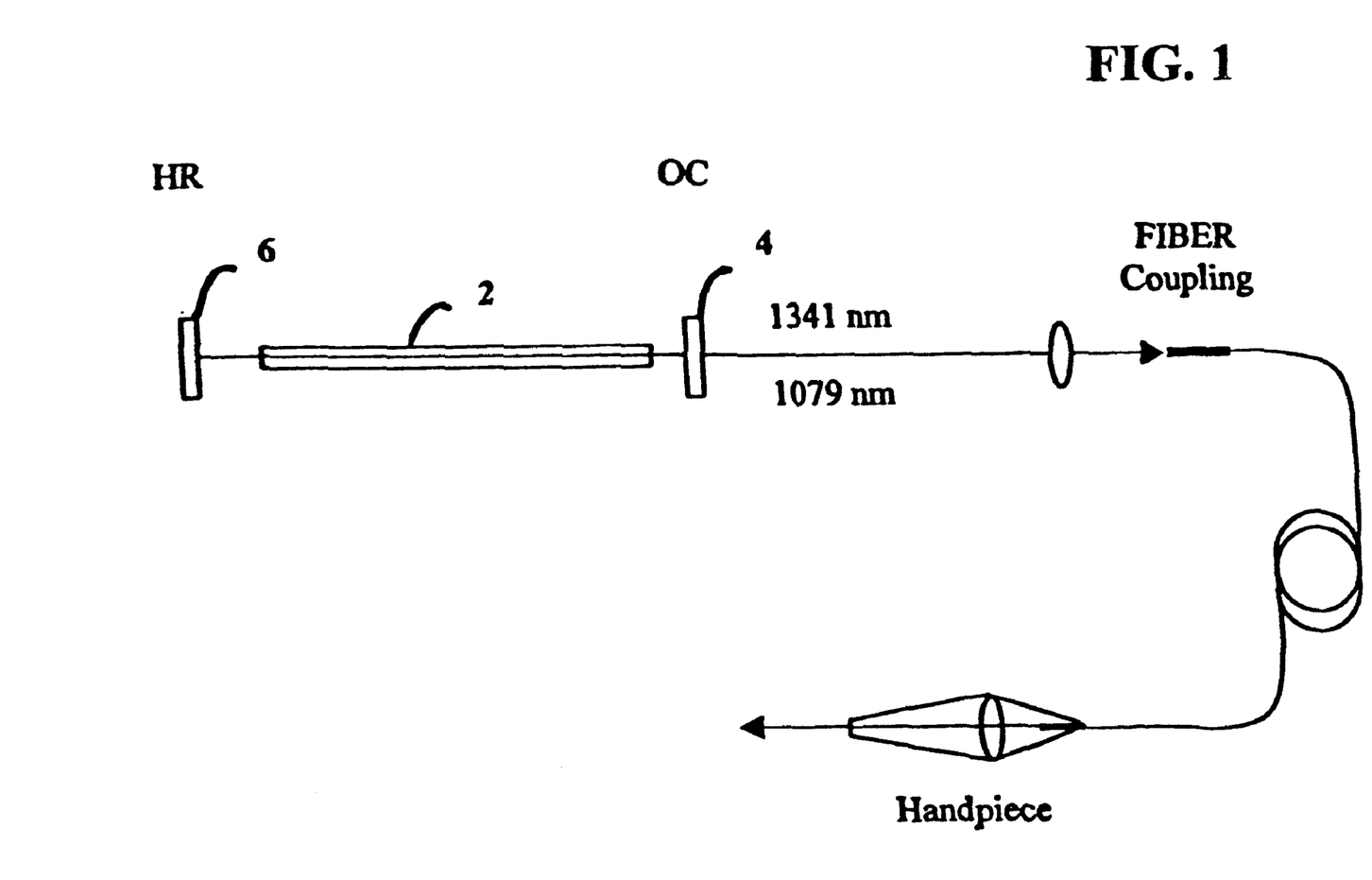
FIG. 1 is a drawing showing the principal features of a preferred embodiment of the present invention.

A first preferred embodiment of the present invention is shown in FIG. 1.

A pulsed laser beam is produced with a YAP:Nd crystal rod 2. Crystal rod 2 is pumped with a pump source (in this case a flash lamp, not shown) driven by a power supply, also not shown. An output coupler 4 is specially coated to partially reflect at both 1341 nm and 1079 nm to produce a laser beam with both wavelengths. The output coupler 4 and a maximum reflectance mirror 6 define the laser resonant cavity. Pulse durations are from about 10 to 20 milliseconds. The configurations should preferably be designed for operator selected pulse rates between 0.5 Hz and 100 Hz. In typical operation the laser is operated in bursts of pulses with each burst containing several pulses (such as 3 to 15 pulses) at selected pulse repetition rates. Preferably the controls are configured so that the operator can select a burst repetition rate up to about 2 Hz. Thus the operator could select a pulse repetition rate of 100 Hz with 5 pulses per burst and a burst repetition rate of 2 Hz. This would provide 10 pulses per second.

Figure 7:
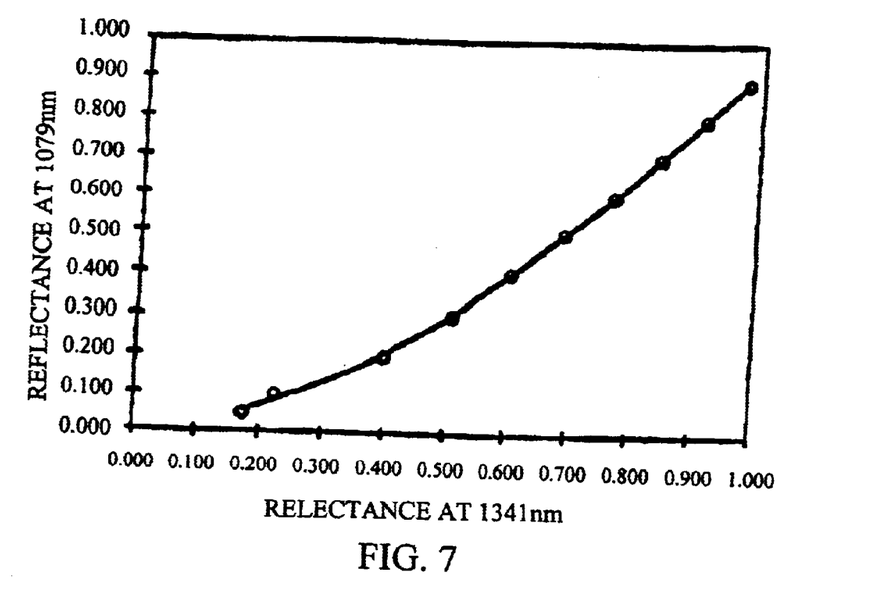
FIG. 7 is a graph of mirror reflectances for simultaneous lasing.

The high reflectivity mirror HR should have reflectance more 99.5% at both wavelength 1079 nm and 1341 nm. The output coupler mirror has a special coating enabling simultaneous lasing at 1079 and 1341 nm. It lies in the range 90–5% for 1079 and 97–17% for 1341 nm. The ratio of reflectivity should be chosen based on the plot FIG. 7 or calculated by the following formula:

$$\ln(1/R_1) = 2L((\sigma_1 v_2 / \sigma_2 v_1)\alpha_2 - \alpha_1) + \sigma_1 v_2 / \sigma_2 v_1 \ln(1/R_2)$$

where:

$R_1$ and $R_2$ are the reflectivity of the mirror at 1079 and 1341 nm, and $\sigma_i$, $v_i$ and $\alpha_i$ are stimulated emission cross section, frequency of the transition and passive loss in crystal all corresponding to two wavelengths.

Figure 2A:
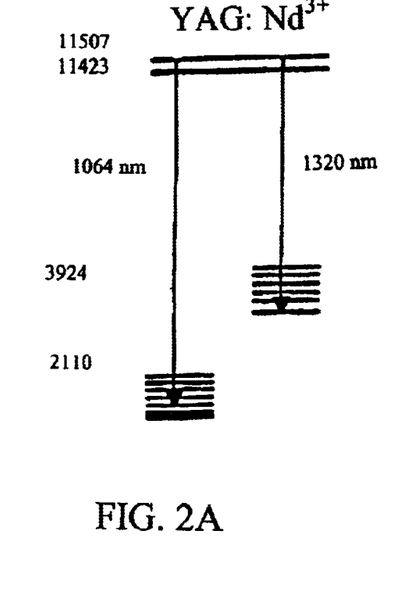
FIGS. 2A and 2B are energy level diagrams
Figure 2B:
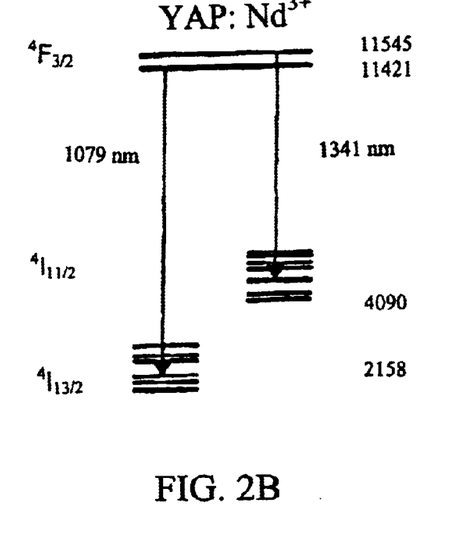

Stimulated emission cross sections in the YAP crystal is $4.6 \times 10^{-19}$ cm$^{-2}$ for the $^4F_{3/2} - ^4I_{11/2}$ 1079 nm transition and $2.2 \times 10^{-19}$ cm$^{-2}$ for the $^4F_{3/2} - ^4I_{13/2}$ 1341 nm transition. The single pass linear loss depends on the quality of crystal. In this example they are taken to be 0.004 cm$^{-1}$ and 0.005 cm$^{-1}$ at 1079 and 1341 nm, respectively. FIGS. 2A and 2B illustrate the structure of laser levels of Nd$^{3+}$ ion in YAG and YAP crystals. In the Nd:YAP crystal the upper laser level for 1079 nm and 1341 nm lines are significantly separated. This in part accounts for less competition between the two laser lines of the Nd:YAP crystal in comparison with Nd:YAG crystal. As a result simultaneous lasing at two wavelengths in YAP crystal is more efficient and easier to achieve. For approximately equal output intensities at each of the two wavelengths, reflectivities of the output couple mirrors should be about 40% for 1079 nm and about 80% for 1341 nm. Reflectivity of the high reflector mirror should be high at both wavelengths. In order to decrease losses of the laser light in the delivery system all transmission elements should preferably have special coatings to minimize reflectivity at 1079 nm and 1341 nm.

Changing the Ratio without Changing the OC

In the output of such a laser it is possible to change the ratio between 1079 and 1341 nm without changing the output coupler. One way is to introduce a dichroic linear absorbing filter or a polarizing filter in the beam train. The dichroic or polarizing filter is preferably placed in the handpiece. This enables the operator to switch wavelength just by changing a filter in the handpiece to a filter most suited for specific application. Or separate handpieces, each with different filters could be provided.

Surface Cooling

Fluencies in excess of 50 J per cm$^2$ when applied in a short period can cause severe damage to the skin surface. However, damage can be avoided or minimized with prior, simultaneous or immediately subsequent cooling of the skin surface. In this preferred embodiment skin surface cooling is provided by the cooling device shown in FIGS. 6A and B which provides prior simultaneous and subsequent cooling. A short description is provided below. Another such device is described in U.S. Pat. No. 6,059,820 which is incorporated herein by reference.

Figure 6A:
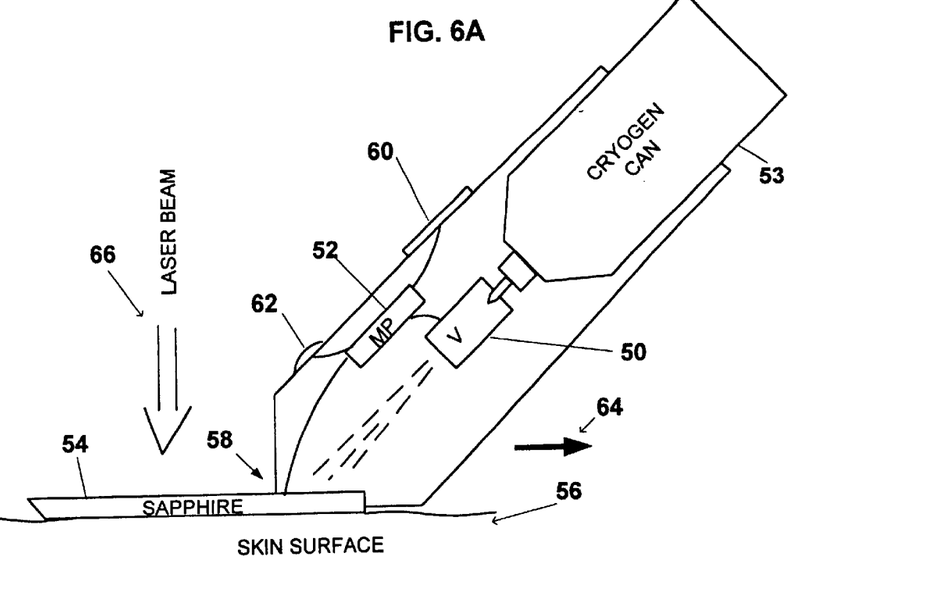
FIGS. 6A and 6B are drawings of a skin cooling device.
Figure 6B:
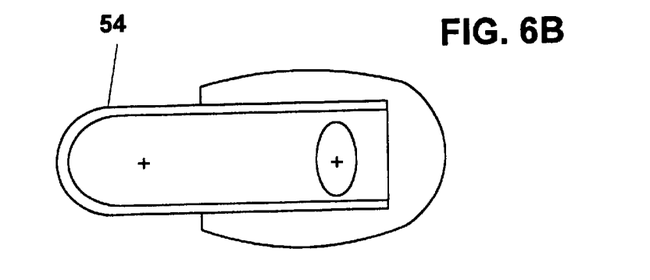

In the FIGS. 6A and B device sapphire cooling window 54 is cooled by a spray from a liquid nitrogen can 53 through valve 50 controlled by microprocessor 52. A thermocouple 58 provides a temperature signal that is converted into a temperature value by microprocessor 52 for display on monitor 60. An off-on button is 62. In a preferred procedure the operator slides the cooling device in direction 64 along the skin surface with one hand and applies laser pulses with applicator 70 using the other hand. Surface cooling can also be provided with an evaporating spray such as liquid nitrogen, air or tetrafluoroethane.

Cooling device 80 protects the surface from damage and portions of the skin below about 1 mm are not damaged because the penetration below 1 mm is not substantial. With this technique tissue at depths in the range of about 1 mm are damaged. For hair removal procedures these damaged tissues include the hair follicle and the blood vessels feeding the hair vessels. The body's immune system operates to repair the damage to the skin tissue creating scar tissue but a large fraction of the hair follicles in the treated region are permanently destroyed. Since the surface tissue is protected by the cooling device and not damaged, no scaring is visible.

Second Preferred Embodiment

If simultaneous lasing at 1079 nm and 1341 nm is not desired the two wavelengths could be obtained separately from one crystal in one laser box. To do this the output coupler is provided with two additional mirrors. One is specifically made to reflect very preferentially at 1079 nm. The other is specifically made to reflect very preferentially at 1341 nm. A special output mirror holder is provided so that these mirrors can be interchanged, for example by linear translating or rotating. In order to make this approach workable, special requirement for mirror mount should be met. The angular misalignment of laser resonator should be not worse than 10 arc second after changing mirrors. These kind of mirror holder are available from Newport Corporation with offices in Irvine Calif. This second preferred embodiment is described in FIGS. 3A, 3B and 3C. In this case the output coupler device 32 is a rotating output coupler which comprises a first partially reflecting mirror 32A coated to reflect light at 1079 nm at about 40 percent and a second partially reflecting mirror 32B coated to reflect light at 1341 at about 70 percent and reflecting 1079 nm light at less than 10 percent. For this embodiment the maximum reflecting mirror unit 34 at the other end of the resonant cavity also comprises two mirrors which are maximum reflecting mirrors at the corresponding wavelengths of 1079 nm and 1341 nm. Alternatively, a single broad-band reflecting mirror could be used.

Dispersion Selection of Single Lines

Figure 8:
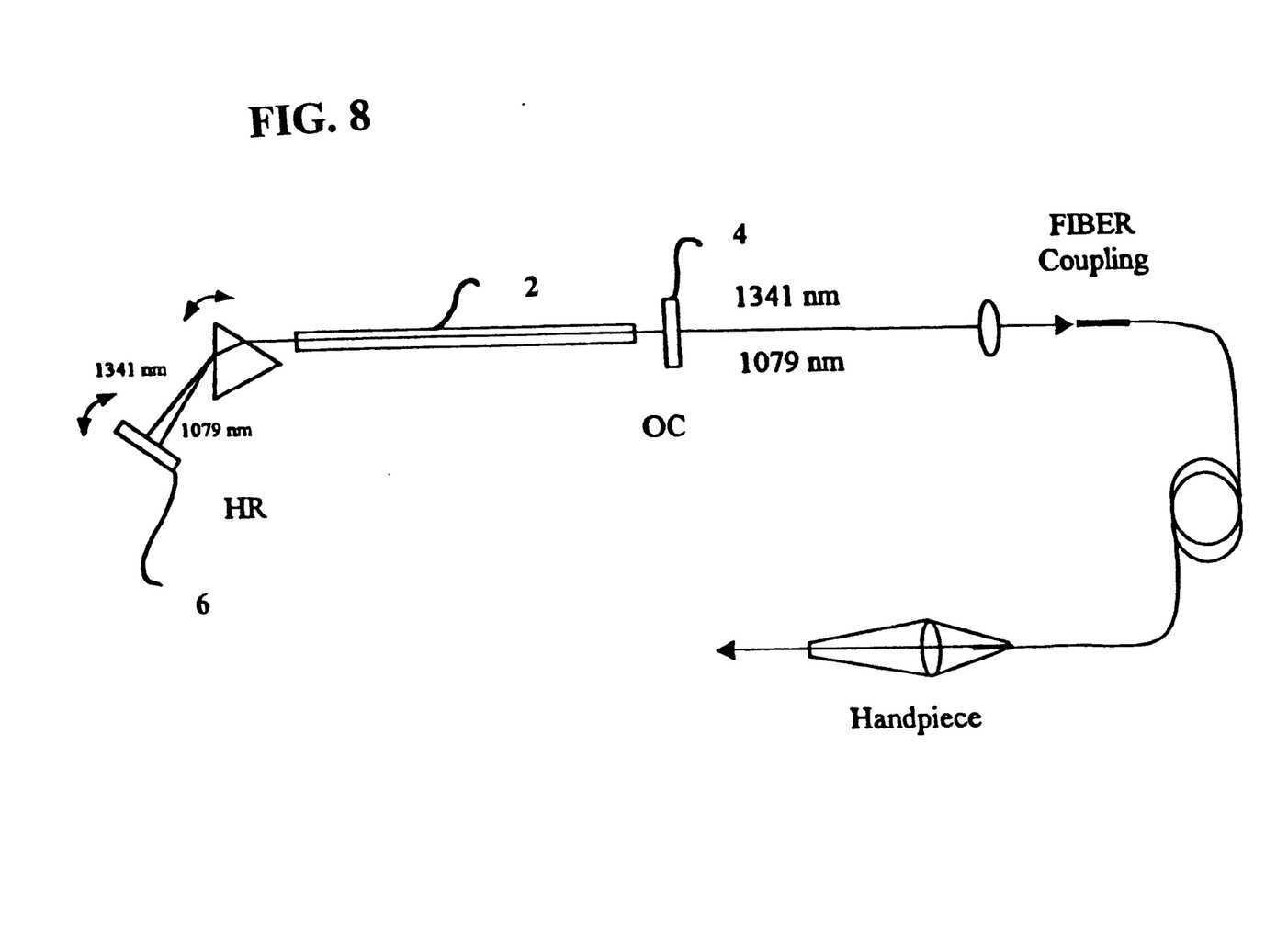
FIG. 8 is a preferred embodiment of the present invention for producing a single selected wavelength beam.

Single lines can also be selected using the technique shown in FIG. 8. A prism is placed between crystal 2 and maximum reflection mirror 6. The prism disperses the beam spectrally so that either of the lines can be selected by proper rotation of mirror 6. The prism should be made of a material with high optical dispersion in visible, for example flint-glass.

As it was noted above simultaneous operation on two wavelengths is much easier to achieve in Nd:YAP laser in comparison with Nd:YAG. Based on the approach described above it is possible to enhance laser performance of existing cosmetic Nd:YAG lasers by substituting Nd:YAG crystal with a Nd:YAP crystal of the same dimensions and changing some delivery optics to enable transmittance of both 1079 and 1341 nm laser light. The procedure might be done in the field right in the doctor's office. This procedure will enable a 1064 nm Nd:YAG laser system originally purchased for only hair removal and veins treatment to work also for subsurface skin re-modeling. Also this technique will enable the use of an existing 1320 nm Nd:YAG system originally purchased for subsurface skin resurfacing to perform subsurface skin resurfacing more efficiently (1341 nm is actually better for subsurface skin resurfacing than 1320 nm) and also perform hair removal and vein treatment using 1079 nm beam light.

Second Harmonic

Each of the wavelengths available from the YAP:Nd crystal can be frequency doubled to provide additional wavelengths. Usually there is no need to filter the fundamental wavelength. Both fundamental and second harmonic wavelengths may be used for treatment simultaneously. The 1079 nm Nd:YAP beam and its second harmonic it can be used to treat small facial vein (telangiectasia). The 1340 nm Nd:YAP laser beam and its second harmonic works also on pigmented lesions.

Optical Components

Figure 3A:
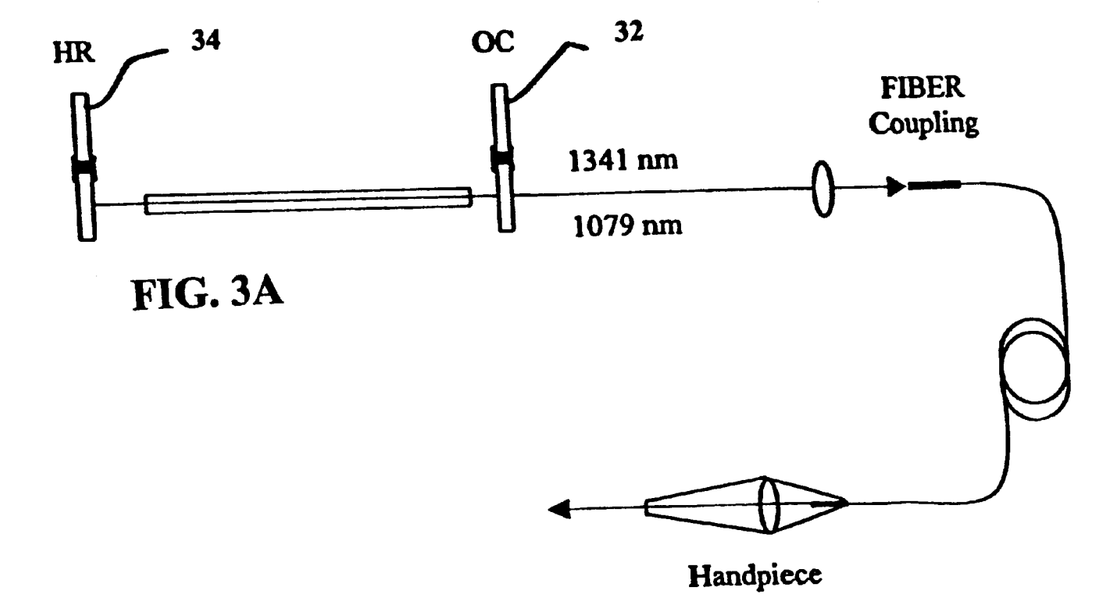
FIGS. 3A, 3B and 3C are drawings of a preferred embodiment of the present invention.
Figures 3B, 3C:
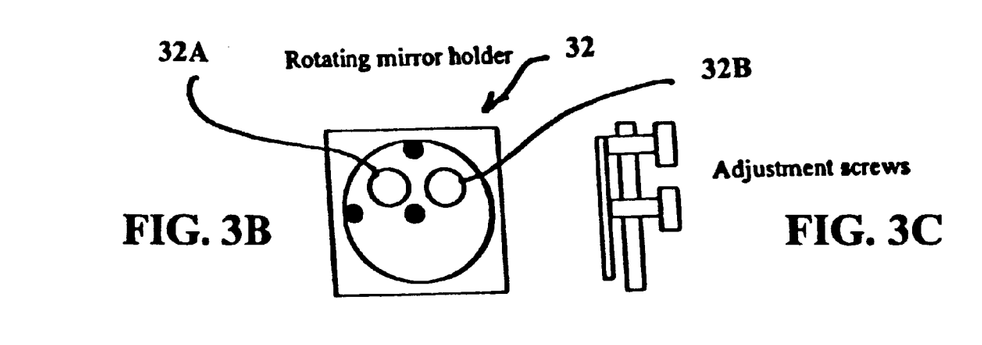

The various optical components needed to fabricate the laser system described above are available from normal optics suppliers and techniques for arranging the components are well known to persons skilled in the laser-optics art. For example the YAP:Nd and YAP:Er rods for production of the 1079 and 1341 nm beams are available from Crytur, Ltd. with offices in Palackeho 175, 51101 Turnov, Czeck Republic and Scientific Material Corp. with offices in Bozeman, Mont. To obtain output energy described above the preferred dimensions of YAP laser rods are 5×127 mm. Pump chamber for YAP:Nd lasers rods are available from Kigre Inc., Hilton Head Island, S.C. or LMI Corporation, Las Vegas, Nev. Optics for arranging the resonator cavities are available from CVI Corp. with offices in Albuquerque, N. Mex. Flash lamp pumps for these crystal rods are Xe flash lamps, for example model L8524 available from Perkin Elmer with offices in Sunnyvale, Calif. A power supply to drive flash lamps is available from Nada Electronics, UK or ASTEX Inc. with offices in Woburn, Mass. Mirrors 4, 6, 32A and 32B shown in FIGS. 1 and 3 are available from CVI Corp.

Preferred Specifications

The power supply and the flash lamp pump source and crystal rod should be sized for pulse energies of 22 J per pulse. Energies per pulse at the other wavelengths are preferably about 4 J. The beam diameters prior to coupling into the optical fiber optic should be about 3 mm or more. The beams are normally focused onto the skin surface to produce fluences in the range of about 30 to 90 J per $cm^2$ during short treatment period. Fluencies in excess of 50 per $cm^2$ could cause severe skin damage. However, as indicated above, damage can be avoided or minimized with prior, simultaneous or immediately subsequent cooling.

Treatment Wavelengths

With this one laser system a large variety of laser treatments can be provided. The wavelength 1079 nm is some absorbed in melanin and only slightly absorbed in oxyhemoglobin and water. Thus, this beam is preferred for hair removal and treatment of larger veins. The 1341 nm wavelength is more highly absorbed in water than the 1079 nm wavelength so the 1341 nm beam is good for dermis collagen remodeling, skin rejuvenation, cartilage reshaping, small vein treatment and microsurgery. Beams with the combination of 1079 nm and 1341 nm beams wavelengths work well for treatment of hair removal, skin rejuvenation and treatment of larger blood veins. A good treatment for subsurface collagen shrinkage for wrinkle removal, stretch mark and keloid scar treatment, cartilage reshaping is to use 1341 nm combined with deep heating of the reticular dermis with 1079 nm. Skin surface cooling before, during and after is preferred.

Microsurgery of skin lesions is performed with 1341 nm laser beams for warts, candelomas, skin tags, etc. and other pathologies (such as tumors, intestine and stomach polyps, vocal cord calcification, uterine cervix lesion ablation, etc), Preferably no cooling is provided with these procedures.

Figure 4:
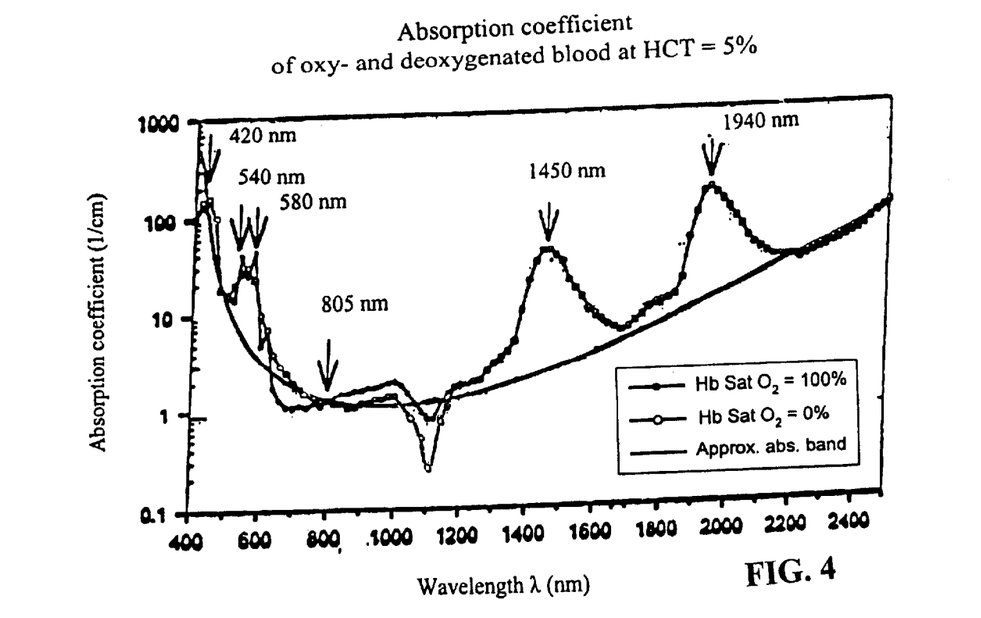
FIG. 4 is a graph of absorption coefficient v wavelength for blood.
Figure 5:
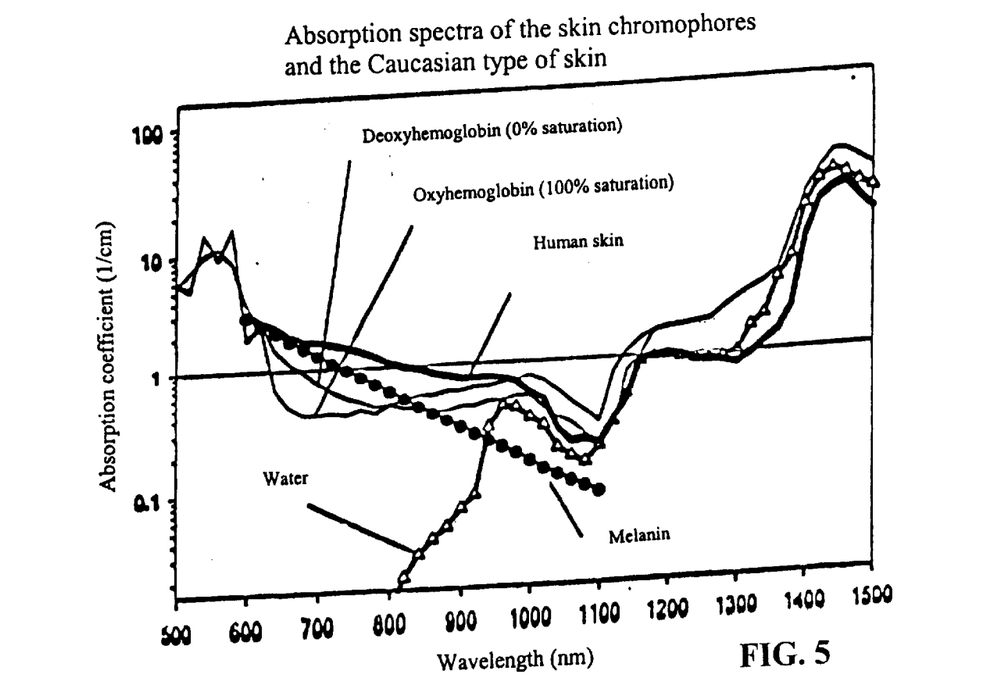
FIG. 5 is a graph of absorption coefficient v wavelength for Caucasian skin.

The 1079 nm wavelength by itself is a preferred wavelength for small (up to 3 mm) veins and hair removal by uniform tissue coagulation. This 1079 nm wavelength is more effective than 1064 nm because its oxyhemoglobin absorption is 42 percent closer to the minimum oxyhemoglobin spike at 1100 nm as shown in FIGS. 4 and 5. This means that blood in large vessels are heated more uniformly as compared to a wavelength which is strongly absorbed in blood in which case a shield can be created at the edge of the vessel nearest the skin surface.

One of the preferred embodiments of the simultaneous dual wavelength applications is a treatment of cancer tumors in the skin. Fast proliferating cancer cells locate at the superficial layers of the skin while blood supply vessels (including those supplying the cancer cells) locate in the deeper layers of the skin. If skin is not cooled, the laser light at 1341 nm can destroy cancer cells at the surface. The more deeply penetrating light at 1079 nm can destroy the blood supply vessels. The destruction of tiny blood vessels feeding a tumor is a key to the successful destruction of the tumor. The dual action of this laser light will destroy tumor more effectively and reliably than a single wavelength radiation.

Other Light Sources

This basic concepts of this invention can be practiced with light sources other than YAP:Nd lasers. An alternate approach is to use flash lamps as sown in FIGS. 9A and 9B. It comprises a flash lamp 22 with collimating reflector 21 and the power supply 11. A non-transparent shield 15 is used to initially divide two separate wavelength ranges, both of which are produced by flash lamp 22. A filter 23 is used to produce light centered around 980 nm+/−180 nm from the one part of the flash lamp. Another filter 24 is used to produce light centered around 1400 nm+/−200 nm from the same lamp. Optical system 25 is used to focus the light from the two parts of the flash lamp into one spot 26.

Figure 9A:
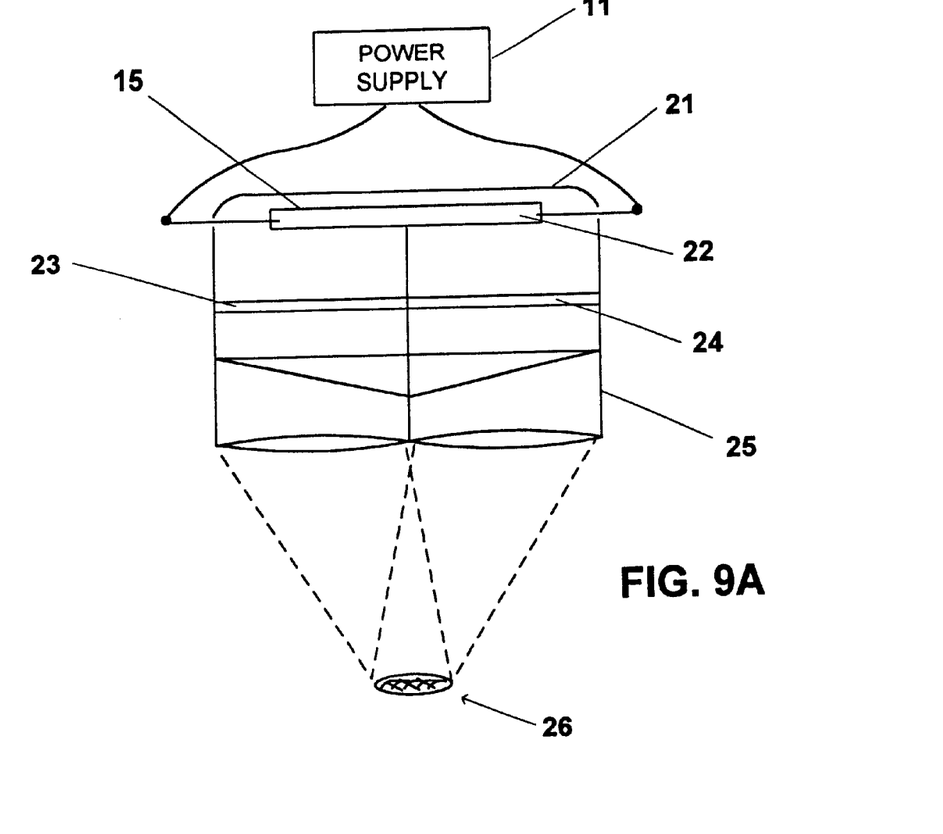
FIGS. 9A and 9B are drawings of a preferred embodiment of the present invention.
Figure 9B:
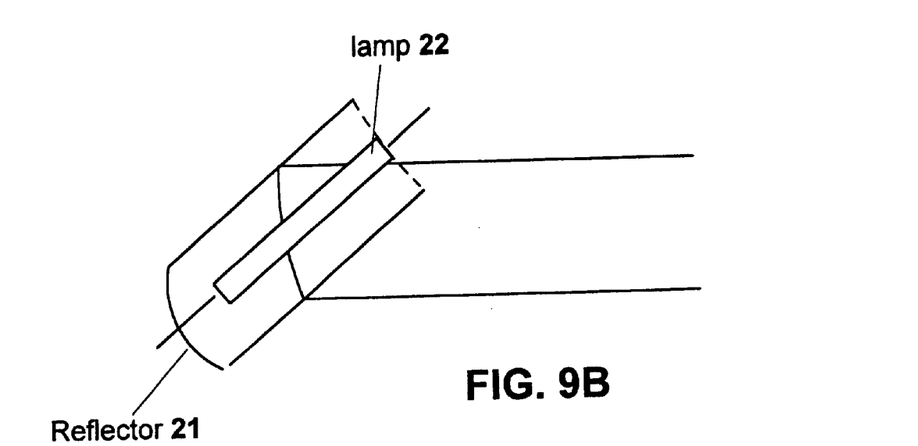

The power supply should be sized to get about 8 J of light energy in each part. The ratio light energy between those two parts may range from 0.1 to 10. The light pulse durations are from about 20 to 200 milliseconds. The configurations should preferably be designed for operator selected pulse rates between 0.5 Hz and 5 The spot size should be 3–6 mm. The working light fluence is preferably 10–120 J/$cm^2$. Other elements of the system are the same as described with respect to the laser sources. Another approach includes a diode laser bar with several different diode chips on it. One laser diode chip could be in the range 850+/−150 nm, another 1000 nm+/−150 nm and the third at 1500 nm+/−200 nm. The light from individual chip is preferably coupled into a fiber and all fibers are connected into a three-duct bundle. The light from laser diode goes through the bundle to the hand piece and the treatment site.

The power supply should be sized to get about 10 W of light energy in each diode chip. The ratio between power of individual diode chip could be from 0.1 to 10. The light pulse durations are from about 0.1 to 0.5 seconds. The configurations should preferably be designed for operator selected pulse rates between 0.5 Hz and 2 Hz. The spot size should be 3–6 mm. The working light fluence 10–120 J/$cm^2$.

The laser diodes could be obtained from SLI Corporation with office at Binghamton, N.Y.

Although the present invention has been described in terms of preferred embodiments the reader should understand many changes and additions could be made without changing the nature of the invention. Therefore, the scope of the invention is to be determined by the appended claims and their legal equivalents.

We claim:

1. An aesthetic medical laser system for producing a twin light output laser beam for skin treatment comprising:
   A) a gain medium comprising an excitable YAP:Nd crystal,
   B) a resonant cavity including said gain medium and comprising a first reflecting optic and an output coupler configured to partially reflect light at 1079 nm and 1340 nm in proportions such that the output laser beam comprises 1079 nm light and 1340 nm light having an intensity ratio; $I_{1079\ nm}$ to $I_{1340\ nm}$, in the range of 0.1 to 10.

2. A laser system as in claim 1 and further comprising an optical wave-guide having a first end connected to the resonant cavity for transmitting said output beam.

3. A laser system as in claim 2 and further comprising a hand piece connected at a second end of said optical wave-guide.

4. A process for treating human skin comprising the steps of:
   A) irradiating said skin with light at a first range of wavelengths and a second range, of wavelengths, both ranges of wavelengths being substantially different and produced by a single device,
   B) controlling energy in said first and second range of wavelengths to produce fluences on the skin in the range of 30 to 90 J per $cm^2$.

5. A process as in claim 4 wherein said device comprises a YAP:Nd laser.

6. A process as in claim 4 wherein said device is an incoherent light source comprising:
   A) a flash lamp,
   B) a reflector light shield, filters, focusing system providing an output beam comprising 980+/−180 nm light and 1400+/−200 nm light having an intensity ratio, $I_{980\ nm}$ to $I_{1400\ nm}$, in the range of 0.1 to 10.

7. A process as in claim 4 wherein said device is a light source comprising:
   A) a bar with at least 3 laser diode chips and
   B) a coupling fiber associated with each said laser diode and bundled to deliver an output laser beam to a handpiece, said output laser beam comprising 850+/−150 nm, 1000 nm+/−150 nm, 1500 nm+/−200 nm light having intensity ratios, $I_{850\ nm}:I_{1000\ nm}:I_{1400\ nm}$, in the range of 0.1 to 10.

* * * * *